United States Patent [19]

Heavner

[11] 4,298,523

[45] Nov. 3, 1981

[54] METHODS AND COMPOSITIONS FOR PREPARATION OF H-ARG-X-Z-Y-TYR-R

[75] Inventor: George Heavner, Flemington, N.J.

[73] Assignee: Ortho Pharmaceutical Corporation, Raritan, N.J.

[21] Appl. No.: 160,241

[22] Filed: Jun. 17, 1980

[51] Int. Cl.$^3$ ............................................. C07C 103/52
[52] U.S. Cl. ............................................. 260/112.5 R
[58] Field of Search ................................. 260/112.5 R

[56] References Cited

U.S. PATENT DOCUMENTS 4,190,646   2/1980   Goldstein et al. ........... 260/112.5 R Primary Examiner—Delbert R. Phillips
Attorney, Agent, or Firm—Geoffrey G. Dellenbaugh

[57] ABSTRACT

Solution phase methods and compositions for preparing H-ARG-X-Z-Y-TYR-R wherein X is LYS and Y is VAL or X and Y are both SAR, Z is ASP or GLU, and R is NH$_2$ or OH.

8 Claims, No Drawings

METHODS AND COMPOSITIONS FOR PREPARATION OF H-ARG-X-Z-Y-TYR-R

BACKGROUND OF THE INVENTION

1. Field of the Invention

The present invention relates to methods for preparing useful peptides, and more particularly to solution synthesis methods for preparing H-ARG-X-Z-Y-TYR-R and to compositions useful therein.

2. Description of the Prior Art

In U.S. Pat. No. 4,190,646 and U.S. Pat. application Ser. No. 124,959, filed Mar. 13, 1980, there are disclosed various peptides which are useful in thymic function and immunological areas. The patent discloses the "thymopoietin pentapeptide" (TP5) and substituted derivatives thereof, while the application discloses peptide analogs of TP5 which have greater potency than TP5. This patent and patent application are incorporated herein by reference. In the referenced patent and application, the peptides were prepared by solid-phase synthesis techniques commonly described as "Merrifield Synthesis." The patent and application also disclose that classical techniques (i.e., solution synthetic techniques) may be employed to prepare certain of these materials, but no specific classical method or synthetic route was disclosed.

While the solid phase synthetic technique of Merrifield is a convenient one for preparation of small quantities of peptides in the laboratory, it would be impractical and generally uneconomic for preparation of large quantities (e.g., more than about 100 grams) of peptide, for which solution synthetic techniques are more appropriate. Moreover, solution synthesis techniques are generally much less costly than solid-phase techniques due to the much lesser unit cost of certain of the reagents used. Among the large variety of solution synthetic techniques available for use in polypeptide preparation, Applicants have discovered particular synthetic methods which produce the desired peptide conveniently and economically.

SUMMARY OF THE INVENTION

The present invention relates to methods for preparation of H-ARG-X-Z-Y-TYR-R, wherein:

X is LYS and Y is VAL or X and Y are both SAR, Z is ASP or GLU, and R is $NH_2$ or OH.

One of the present methods comprises the steps of:
(a) forming fragment I, which consists of H-Y-TYR-R', as described below;
(b) forming fragment II, which consists of alpha-T-X-omega-U-Z-OH, as described below;
(c) connecting fragment I and fragment II together to form fragment III, which consists of alpha-T-X-omega-U-Z-Y-TYR-R', as described below;
(d) removing the alpha-amino protecting group T to yield fragment IIIA;
(e) adding to fragment IIIA a protected L-arginine moiety (alpha-T-omega-T'-ARG-OH), as described below, to form the protected pentapeptide;
(f) removing the protecting groups; and
(g) isolating and purifying the resulting peptide.

Alternatively, steps b-c above may be replaced by the following steps h-k:
(h) adding a protected Z moiety (alpha-T-omega-U-Z-OH) to fragment I to form fragment IV, which consists of alpha-T-omega-U-Z-Y-TYR-R', as described below;
(j) removing the protective group T from the alpha-amino position of the Z moiety of fragment IV to form fragment IVA;
(k) adding a protected X moiety (alpha-T-X) to fragment IVA to form fragment III, as described below;

In a second alternative route, fragment IVA (H-omega-U-Z-Y-TYR-R-') is connected to fragment V (alpha-T-omega-T'-ARG-X-OH) as described below. Fragment V may be prepared as described below. This second alternative route avoids the necessity of removing L-arginine impurity from the final product, which is a difficult and sometimes impossible task.

Fragment I may be formed by the steps of:
(i) protecting the alpha-amino group of the Y moiety by allowing it to react with a reagent which will introduce the protecting group T;
(ii) activating the protected Y formed in step (i) with respect to nucleophilic attack at the carboxy group by an amine, to form a carboxy activated protected Y, as further described below;
(iii) reacting said carboxy activated protected Y with TYR-R'; and
(iv) removing the protective group T, whereby fragment I is formed.

Fragment II may be formed by the steps of:
(i) preparing omega-U-Z-OH, wherein U is protecting group on the omega carboxy group of the Z amino acid;
(ii) protecting the alpha-amino group of X amino acid by allowing it to react with a reagent which will introduce the protecting group T in such a manner as to specifically protect the alpha-amino group;
(iii) activating the protected X amino acid formed in step ii) with respect to nucleophilic attack at the carboxy group by an amine, to form a carboxy activated protected X amino acid as further described below; and
(iv) allowing the carboxy activated protected X amino acid described in step (iii) to react with the protected Z amino acid prepared in step (i) to form alpha-T-X-omega-U-Z-OH (fragment II).

Fragment III is formed by activating the Z portion of fragment II with respect to nucleophilic attack at its alpha-carboxy group by an amine and allowing this activated fragment II to react with fragment I.

Fragment V may be formed by the steps of:
(i) protecting the alpha-amino group and the quanidino group of the L-arginine by allowing it to react with reagents which will introduce the protecting groups T and T';
(ii) activating the protected ARG formed in step i) with respect to nucleophilic attack at the carboxy group by an amine, to form a carboxy activated protected ARG, as further described below; and
(iii) reacting said carboxy activated protected ARG with X amino acid, whereby fragment V is formed. Of course, if X is LYS, then its epsilon-amino group must also be suitably protected by the amino-protecting group T" during the preparation of Fragments containing X and their use to prepare the end product peptide. The T" group must be readily removable under conditions which will not destroy the resulting peptide, while being stable during the removal of the T groups.

The alpha-amino protective group T may be the same or different for each amino acid above and should be stable to removal by the steps employed for joining the amino acid groups while still being readily removable at the end of the connecting steps by conditions which will not cleave any of the amide bonds of the peptide. For some groups (e.g., BOC) this removal is caused by strong acid (e.g., trifluoroacetic acid), which results in the deprotected intermediate being obtained as the corresponding acid addition salt (e.g., trifluoroacetate).

The guanidino protective group T' may be any suitable amino protecting group as described below, or a nitro group as well as acid addition salts such as the hydrochloride. Of the amino protecting groups, urethane protecting groups (formula a below) and substituted sulfonic acid derivatives such as p-methoxybenzensulfonyl and tosyl are preferred. The hydrochloric salt is most preferred. This guanidino protective group is referred to herein as "omega" group to indicate that it is at the end of the chain. The exact location of many guanidino protective groups on the chain is not definitely known.

The carboxy-protective group U should be readily removable under conditions which will not destroy the resulting peptide, while being stable during the removal of the T groups. The R' group is either $NH_2$ (for product peptides where R is $NH_2$) or OU (for product peptides where R is OH).

Exemplary of suitable amino-protecting groups are those of formula:

(a)

wherein $R_1$ is aryl (such as phenyl, tolyl, or xylyl); adamantyl; monosubstituted methyl (such as allyl, beta-cyanoethyl, fluoronylmethyl, benzyl, or benzyl wherein the phenyl ring is substituted with from one to three members selected from halo, nitro, loweralkyl, and loweralkoxy); disubstituted methyl (such as diisopropylmethyl, diphenylmethyl, cyclohexyl, cyclopentyl, or vinyl); or trisubstituted methyl (such as t-butyl, t-amyl, dimethyltrifluoromethylmethyl, or dimethylbiphenylmethyl);

(b)

wherein $R_2$ is loweralkyl of two to four carbons such as ethyl, isopropyl, t-butyl, and the like, or loweralkyl of one to four carbons substituted with from one to five halo groups such as trifluoromethyl, chloromethyl, pentachloroethyl, and the like;

(c)

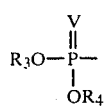

wherein V is S or O and $R_3$ and $R_4$ are each benzyl or loweralkyl;

(d)

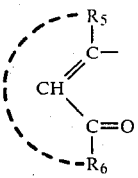

wherein $R_5$ and $R_6$ taken individually are each lowerakyl or $R_5$ and $R_6$ taken together is

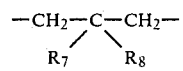

wherein $R_7$ and $R_8$ are each hydrogen or loweralkyl; and (e)

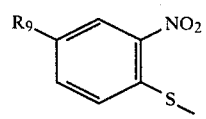

wherein $R_9$ is hydrogen or nitro;

(f)

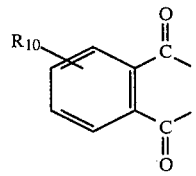

wherein $R_{10}$ is hydrogen, methyl, halo, or nitro.

Amino-protecting group (f), which is bidentate, may be used only for the alpha-amino groups of L-arginine or L-valine or the alpha-amino and epsilon-amino groups of L-lysine but not for the alpha-amino group of sracosine. The amino-protecting group on the sarcosine alpha-amino group must be monodentate due to the methyl substituent on that amino group. The remaining amino protecting groups may be used for all amino acids.

As used herein, "halo" includes fluoro, chloro, bromo, and iodo, but chloro and bromo are preferred. The terms "loweralkyl" and "loweralkoxy" include, respectively, saturated aliphatic hydrocarbons of one to six carbons such as methyl, ethyl, isopropyl, t-butyl, n-hexyl, and the like and the corresponding alkoxies such as methoxy, ethoxy, isopropoxy, t-butoxy, n-hexoxy, and the like. Methyl is the preferred loweralkyl and methoxy is the preferred loweralkoxy.

The reagents employed to introduce these protecting groups (usually the corresponding acid chlorides, although other derivatives may be used) are sometimes referred to herein as "protecting group reagents". Other suitable protective groups are disclosed in, for example, "Protective Groups in Organic Chemistry", J.F.W. McOmie, ed., Plenum Press, N.Y., 1973.

It is preferred that each T and T" be the same and be benzyloxycarbonyl (CBZ) or trifluoroacetyl (TFA). It is preferred that T' be the hydrochloride salt.

A variety of reagents may be employed for producing the carboxy activated protected amino acid residues described above.

One type of carboxy activated protected amino acid residue is a reactive ester. Exemplary of agents used to prepare the suitable active esters are phenol; phenol wherein the phenyl ring is substituted with one to five members selected from halo (e.g., chloro or fluoro), nitro, cyano, and methoxy; thiopheny; N-hydroxyphthalimide; N-hydroxysuccinimide; N-hydroxyglutarimide; N-hydroxybenzamide; 1-hydroxybenzotriazole; and the like. Other suitable agents are disclosed in, for example, "Protective Groups in Organic Chemistry", J.F.W. McOmie, ed. referred to above. The specific examples provided below generally employ N-hydroxysuccinimide or 1-hydroxybenzotriazole.

Other activation methods, such as the mixed or symmetrical anhydride method, the acid chloride method, and the azide method, are well-known in the art, being described in, e.g., Bodanszky, et al., "Peptide Synthesis", 2nd ed., 1976, pp. 85–128. These other methods may also be employed.

For convenience, the following abbreviations are employed herein to refer to the various amino acids:

| Amino Acid | Abbreviation |
| --- | --- |
| L-lysine | LYS |
| L-valine | VAL |
| L-tyrosine | TYR |
| L-aspartic acid | ASP |
| L-glutamic acid | GLU |
| Sarcosine | SAR |
| L-arginine | ARG |

DETAILED DESCRIPTION OF THE INVENTION

One of the present methods is depicted diagrammatically in the following FIG. 1:

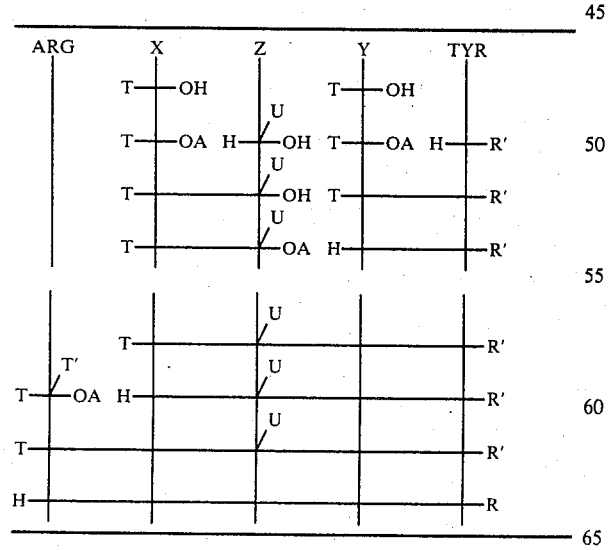

The first alternate method is depicted diagrammatically in the following FIG. 2:

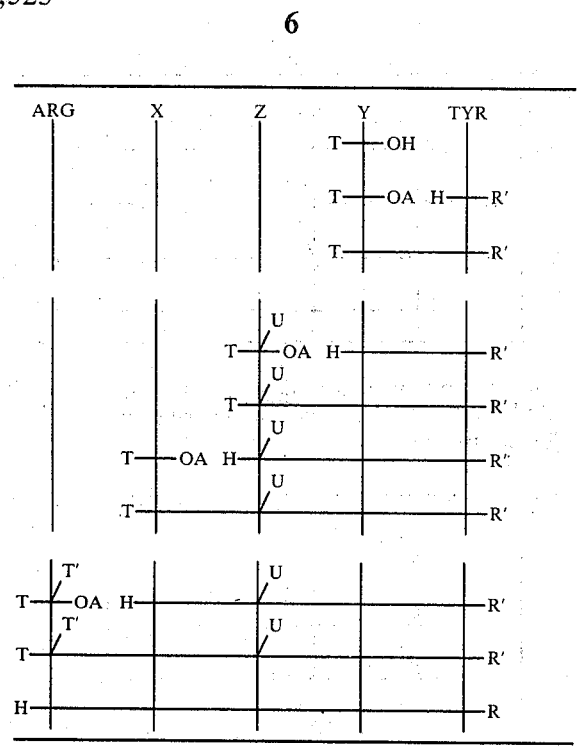

The second alternate method is depicted diagrammatically in the following FIG. 3:

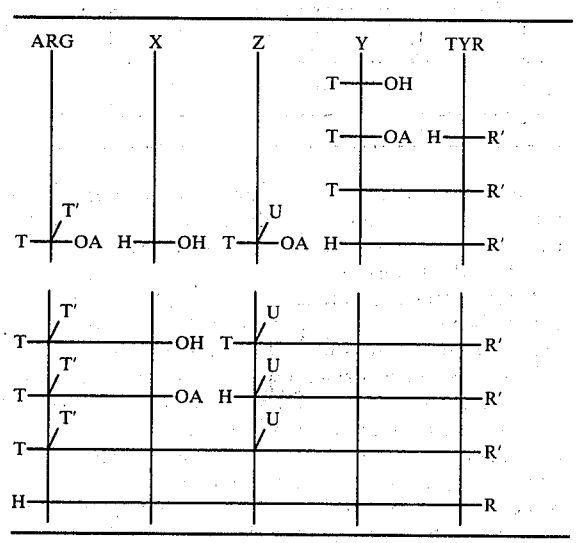

One exemplary preparation of H-ARG-SAR-ASP-SAR-TYR-NH₂ is shown diagrammatically in the following FIG. 4:

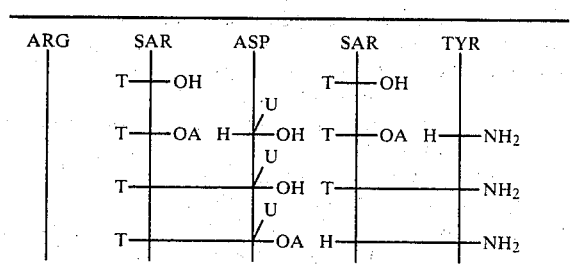

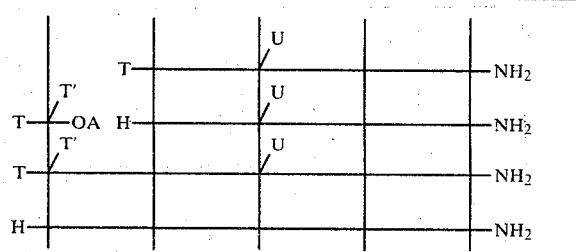

One exemplary preparation of H-ARG-LYS-ASP-VAL-TYR-OH is shown diagrammatically in the following FIG. 5:

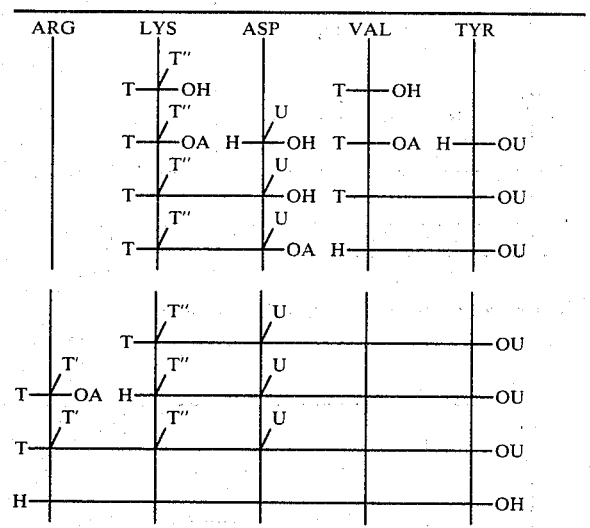

in the above figures the protective groups are represented by U, T, T' and T" as discussed above, while the carboxy activation of the amino acid residues is indicated by the letters "OA".

With reference to the above FIG. 4, fragment I may generally be prepared as follows. In order to protect the amino group of sarcosine, a water-soluble basic addition salt of sarcosine is formed and dissolved in water. Conveniently, this basic addition salt can be formed by dissolving sarcosine in a slight molar excess of sodium hydroxide. To this solution is then simultaneously added a slight excess of a reagent for introducing the protecting group T (e.g., the corresponding acid chloride such as benzyloxycarbonyl chloride) and a solution of base (e.g., sodium hydroxide) to react with the acid (e.g., HCl) formed during the reaction. The protecting group adding reagent may be in solution or neat and is preferably the acid chloride. After reaction is complete, the excess protecting group adding reagent is removed (e.g., by extraction with diethyl ether or any other organic solvent immiscible with water), following which the protected sarcosine is isolated from the unreacted sarcosine by treatment with acid (e.g., hydrochloric acid). The acid treatment converts the basic addition salt of the unprotected sarcosine into an acid addition salt of the unprotected sarcosine, which salt is soluble in water. However, the acid treatment converts the protected sarcosine basic addition salt only into protected sarcosine, since no acid addition salt can be made due to the protected amino group. This protected sarcosine, being insoluble in water, is easily separated from the salt of the unprotected sarcosine, for example by extraction with an immiscible organic solvent as described above. As used herein, the term "immiscible organic solvent" includes all common laboratory organic solvents which do not mix with water, such as for example diethyl ether, ethyl acetate, benzene, toluene, xylene, and the like. The preferred protected sarcosine, N-benzyloxycarbonyl sarcosine, is a known compound. A method for its preparation is shown by R. S. Tipton and B. A. Pawson, J. Org. Chem., 26, 4698 (1961), and the compound is commercially available from Bachem, Inc., Torrance, CA.

In preparation for the condensation of this protected sarcosine with an L-tyrosine amide molecule to form fragment I, the amino-protected sarcosine should usually be activated in some fashion to promote the formation of the bond. While the preferred way of conducting this activation is by formation of an "active ester", it is contemplated that other methods of activation known in the art such as the mixed or symmetrical anhydride, azide, or acid chloride methods could be employed.

It is contemplated that any active ester of the protected sarcosine could be employed; one preferred active ester is that formed by hydroxysuccinimide. The active ester of the protected sarcosine is prepared by reacting equivalent quantities of the protected sarcosine and an active ester reagent in solution of a suitable organic solvent such as, for example, tetrahydrofuran, dioxane, dimethylformamide, pyridine, or the like. To this solution is then added an equivalent amount of a coupling agent, typically dicyclohexylcarbodiimide. While other coupling agents are effective, dicyclohexylcarbodiimide is particularly useful because the by-product of the coupling reaction is very insoluble in the class of solvents used, and therefore may easily be removed by filtration, leaving the coupled product in solution. L-tyrosine amide is commercially available (e.g., from Sigma Chemical Company, St. Louis, MO) or may be prepared by known methods.

The next step in the preparation of fragment I consists of reacting a molar equivalent of the L-tyrosine amide with the protected sarcosine active ester in the presence of one equivalent of a salt-forming material such as an organic tertiary amine. While any organic tertiary amine may be used, triethylamine has been found to work well. The solvent is a suitable organic solvent as described above. The unreacted amino acids are removed by treatment of the reaction mixture with acid (e.g., acetic acid) and separation by extraction with an immiscible organic solvent as described above.

The final step is the removal of the alpha-amino protecting group from the sarcosine, preferably with trifluoroacetic acid, to yield fragment I.

The preparation of fragment II generally starts with L-aspartic acid which is protected on its beta-carboxy group or L-glutamic acid which is protected on its gamma-carboxy group. This beta or gamma-carboxy group is generally referred to as the "omega" group in accordance with accepted nomenclature to indicate that it is at the end of the chain.

Exemplary of suitable carboxyl protecting groups are benzyl and benzyl in which the phenyl group is substituted with from one to three members each selected from halo (e.g., chloro or bromo), nitro, $C_1$-$C_3$ loweralkoxy (e.g., methoxy), or $C_1$-$C_3$ loweralkyl (e.g., methyl). See the above-referenced McOmie text for further description of such groups. Benzyl is preferred. This beta-protected L-aspartic acid and gamma-protected L-glutamic acid are available commercially from Bachem, Inc., Torrance, California, or may be prepared by known methods.

This beta-protected L-aspartic acid or gamma-protected L-glutamic acid (ometa-U-Z) is then allowed to react with the alpha-amino protected sarcosine which has been activated (e.g., by conversion into an active ester) as discussed above, to form Fragment II. On FIG. 4, Z is ASP.

Fragments I and II are joined to form the protected tetrapeptide alpha-T-SAR-beta-U-ASP-SAR-TYR-$NH_2$ (fragment III) by reacting equivalent amounts in a suitable aprotic solvent such a dimethylformamide in the presence of a slight excess of a coupling agent such as dicyclohexylcarbodiimide. It is also preferred to conduct this reaction in the presence of a material which minimizes racemization adjacent to the carboxyl group on the L-lysine portion of fragment I and enhances the rate of reaction, such as for example 1-hydroxybenzotriazole. AS with fragment II, the alpha-amino protecting group on the sarcosine residue of fragment III is removed with trifluoroacetic acid to yield fragment IIIA.

Finally, following a coupling reaction similar to that used to join fragments I and II, an alpha-amino and guanidino protected L-arginine residue is joined to the amino terminus of fragment IIIA which, after removal of all the protective groups, yields the desired pentapeptide amide. The removal of the protective groups may be accomplished, for example, by treatment with hydrogen gas in the presence of a palladium on carbon catalyst in a suitable reducing solvent as described above (preferably aqueous acetic acid). The hydrogen gas need not be under pressure greater than one atmosphere, although the use of pressure is convenient since it accelerates the rate of reduction.

The alternate preparative methods are accomplished in the same general way as discussed above.

That is, in the first alternative route a protected Z moiety is added to fragment I to form fragment IV, which addition may take place by formation of, e.g., an active ester of the protected Z amino acid and allowing the same to react with fragment I in the same fashion that fragment II was allowed to react in the above description. Then, the alpha-amino protecting group on the Z moiety is removed, preferably with trifluoroacetic acid, following which a protected X amino acid is added to fragment IV via, e.g., the active ester route, to produce fragment III.

In the second alternative route, fragment V is prepared by allowing an alpha-amino and guanidino protected L-arginine to react with a molar equivalent of X amino acid in the presence of e.g., 1-hydroxybenzotriazole. Following this, fragment V is joined to fragment IVA in a fashion similar to that used for joining fragments I and II.

The isolation and purification of the resulting impure product may be accomplished by a combination of crystallization and ion exchange chromatography, (preferably using ammonium acetate-pH5 as eluent) using thin-layer chromatography to monitor the identity of the materials in each fraction. While several isolation and purification procedures are given in the following examples, it is clearly contemplated that others could be used.

Also included within the scope of the present invention are compositions useful for practicing the subject methods (e.g., Fragments I, II, III, IIIA, IV, IVA, and V and other intermediates) as well as the protective products.

EXAMPLE I

Preparation of Fragment I: SAR-TYR-$NH_2$

A. BOC-Sarcosine-hydroxysuccinimide ester (BOC-SAR-OSu):

BOC-Sarcosine (24.78 g, 0.13 moles) and N-hydroxysuccinimide (15.5 g, 0.13 moles) were dissolved in 300 ml of dry THF and cooled to $-5°$. A solution of dicyclohexylcarbodiimide (26.98 g., 0.13 moles) in 100 ml of dry THF was added over a period of 15 minutes. The resulting reaction mixture was stirred overnight and allowed to come to ambient temperature. The solid was removed by filtration and the solvent evaporated under reduced pressure to give a white solid. The solid was crystallized from 250 ml of absolute ethanol at 4° to give 32 g (86%) of a white solid, m.p. 121°–123°.

Anal: Calcd: C, 50.35; H, 6.34; N, 9.79. Found: C, 50.23; H, 6.44; N, 9.67.

TLC: Rf=0.81, $CHCl_3$/MeOH 9/1 (Silica Gel G, 250 micron).

p.m.r. ($\delta$, $CDCl_3$): 1.45, S, 9H, BOC; 2.83, S, 4H, —OSu; 2.93, S, 3H, N—$CH_3$; 4.27, S, 2H, —$CH_2$—.

M.S.: M+286

B. BOC-Sarcosyl-L-Tyrosine amide (BOC-SAR-TYR-$NH_2$):

L-Tyrosine amide (2.17 g, 10 mmoles) and triethylamine (1.01 g, 10 mmoles) were dissolved in 25 ml of dry methanol. BOC-Sarcosine hydroxysuccinimide (2.86 g, 10 mmoles) was added and the reaction mixture stirred overnight at ambient temperature. The volatiles were removed under reduced pressure and the residue partitioned between EtOAc (50 ml) and NaCl solution [50 ml (25 ml $H_2O$+25 ml saturated NaCl)]. The phases were separated and the organic phase washed twice more with the same composition NaCl solution and then dried with $MgSO_4$. The drying agent was removed by filtration and the solvent evaporated under reduced pressure. The residue was chromatographed on a 75 g, 1" column of Silicar CC7 using ethylacetate as an eluent. The compound began to appear at 390 mls. The next 475 ml were collected and evaporated to give 1.55 g (44%) of a white solid.

Anal: Calcd: C, 58.11; H, 7.17; N, 11.96. Found: C, 57.96; H, 6.96; N, 11.45.

TLC: (Silica Gel GF) $R_f$=0.46 $CHCl_3$/MeOH 9/1.

C. Sarcosyl-L-Tyrosine amide, trifluoroacetate (TFA SAR-TYR-$NH_2$):

BOC-Sarcosyl-L-Tyrosine amide (1.30 g, 3.7 mmoles) was dissolved in 15 ml of trifluoroacetic acid at 0°. The solution was stirred for one hour at 0° and the solvent removed under reduced pressure. The resulting oil was triturated with 50 ml of anhydrous ether to give 1.27 g (94%) of a white solid.

p.m.r. ($\delta$, $CD_3OD$): 2.3, S, 3H, N—$CH_3$; 3.00, d, 2H, —$CH_2$—C—; 3.7, S, 2H, —N—$CH_2$—C=O; 6.9; q, 4H, aromatic

EXAMPLE II

Preparation of Fragment II:
BOC-SAR-beta-benzyl-ASP
(BOC-Sarcosyl-beta-benzyl-L-Aspartic acid)

Triethylamine (2.02 g, 20 mmoles) and beta-benzyl-L-Aspartic acid (2.23 g, 10 mmoles) were stirred in 50 ml of dry THF. BOC-Sarcosine-hydroxysuccinimide ester (2.68 g, 10 mmoles) was added and the solution stirred at ambient temperature overnight. Solids were removed by filtration and the solvent removed under reduced pressure. The residue was partitioned between ethyl acetate (100 ml) and 2N HCl (100 ml). The phases were separated and the organic phase washed with water (2×100 ml), saturated NaCl solution (1×100 ml) and dried (MgSO$_4$). The drying agent was removed by filtration and the solvent was removed under reduced pressure. The residue was triturated with hexane. The hexane was decanted and the residue dried under reduced pressure to give 2.64 g (67%) of a hygroscopic solid.

TLC: R$_f$=0.73+trace impurity at 0.48; CHCl$_3$/MeOH/HOAc 85/10/5; (Silica Gel G, 250 micron).

p.m.r. (δ, CH$_3$OD): 1.45, S, 9H, BOC; 2.82, S, 3H, N—CH$_3$; 2.95, M, 2H, —C$\underline{H}_2$—C; 3.85, S, 2H, —N—CH$_2$—C=C=O; 4.85, t, 1H, —CH—; 5.08, S, 2H, —C$\underline{H}_2$; 5.46, S, 2H, —NH+—CO$_2$H; 7.3, S, 5H,—φ [α]$_D$17° = +13.3°(C=1.032, MeOH)

EXAMPLE III

Preparation of Fragment III:
BOC-Sarcosyl-beta-benzyl-L-Aspartyl-Sarcosyl-L-Tyrosine amide
(BOC-SAR-beta-Bzl-ASP-SAR-TYR-NH$_2$)

BOC-Sarcosyl-beta-benzyl-L-Aspartic acid (0.52 g, 1.3 mmoles) and 1-Hydroxybenzotriazole monohydrate (0.18 g 1.3 mmol were dissolved in 10 ml of dry DMF and the solution cooled to 0°. Dicyclohexylcarbodiimide (0.27 g, 1.3 mmoles) in 7.5 ml of dry DMF was added and the resulting solution stirred for 1 hour at 0°. Sarcosyl-L-Tyrosine amide, trifluoroacetate (0.50 g, 1.3 mmoles) and diisopropylethylamine (0.17 g, 1.3 mmoles) were dissolved in 5 ml of dry DMF and immediately added to the first solution. The reaction was stirred overnight and allowed to each ambient temperature. The solid was removed by filtration and the residue dissolved in 25 ml of ethylacetate. The organic phase was washed in succession with 10% citric acid (2×25 ml), water (2×25 ml), 5% NaHCO$_3$ (2×25 ml), H$_2$O (2×25 ml), saturated NaCl (25 ml) and dried over anhydrous MgSO$_4$. The drying agent was removed by filtration and the solvent was removed under reduced pressure to give 0.6 g (73.5%) of a white solid.

TLC: R$_f$=0.31; CHCl$_3$/MeOH 9/1; (Silica Gel G, 250 micron).

p.m.r. (δ, CDCl$_3$): 1.45, S, 9H, BOC; 2.95, m, 10H, 2×N—CH$_3$, —CH$_2$—C$\underline{H}$ (Asp), —CH$_2$—CH (Tyr); 3.8, m, 4H, 2×N—CH$_2$—C=O; 4.6, m, 2H, —C$\underline{H}$—CH$_2$, Asp, —C$\underline{H}$—CH$_2$—(Tyr); 5.1, m, 2H, —CH$_2$—φ; 6.92, q, 4H, tyrosine aromatic; 7.25, S, 5H, aromatic benzyl [α]$_D$21° =12.4° (C=0.1046, MeOH)

Anal: Calcd for C$_{31}$H$_{41}$N$_5$O$_9$: C, 59.32; H, 6.58; N, 11.16. Found: C, 58.73; H, 6.80; N, 10.76.

EXAMPLE IV

Preparation of Fragment IIIA:
Sarcosyl-beta-benzyl-L-Aspartyl-Sarcosyl-L-Tyrosine amide, trifluoroacetate (TFA SAR-beta-Bzl-ASP-SAR-TYR-NH$_2$)

BOC-Sarcosyl-beta-benzyl-L-Aspartyl-Sarcosyl-L-Tyrosine amide (0.48 g, 0.76 mmoles) was dissolved in 10 ml of TFA at 0° and stirred at 0° for one hour. The solvent was removed under reduced pressure and the residue triturated overnight with 50 ml of anhydrous ether. The suspension was filtered and the solid washed well with ether and dried under vacuum to give 0.4 g (82%) of a white solid.

TLC: R$_f$ =0.56; n-BuOH/HOAc/H$_2$O; (Silica Gel GF).

EXAMPLE V

Preparation of pentapeptide

A. Alpha-Phenylmethoxycarbonyl-L-Arginyl(HCl)-Sarcosyl-beta-benzyl-L-Aspartyl-Sarcosyl-L-Tyrosine amide [CBZ-ARG(HCl)-SAR-beta-Bzl-ASP-SAR-TYR-NH$_2$]

Alpha-Phenymethoxycarbonyl-L-Arginine HCl (2.66 g, 7.8 mmoles) and 1-hydroxybenzotriazole monohydrate (1.06 g, 7.8 mmoles) were dissolved in 20 ml of dry dimethylformamide and cooled to 0°. Dicyclohexylcarbodiimide (1.61 g, 7.8 mmoles) was dissolved in 5 mls and added to the first solution. The resulting reaction mixture was stirred for 1 hour at 0°. The TFA salt of Sarcosyl-beta-benzyl-L-Aspartyl-Sarcosyl-L-Tyrosine amide (5.0 g, 7.8 mmols) was dissolved in 15 mls of dry DMF with triethyl amine (0.79 g, 7.8 mmoles) and added to the first solution. The reaction was stirred overnight and allowed to reach ambient temperature. The solid was removed by filtration and the volatiles removed under reduced pressure. The residue was triturated with water to give a residue (3 g).

TLC: R$_f$=0.60; n-BuOH/HOAc/H$_2$O 3/1/1; (Silica Gel GF).

B. L-Arginyl-Sarcosyl-L-Aspartyl-Sarcosyl-L-Tyrosine amide (ARG-SAR-ASP-SAR-TYR-NH$_2$)

Alpha-Phenylmethoxycarbonyl-L-Arginyl(HCL)-Sarcosyl-beta-benzyl-L-Aspartyl-Sarcosyl-L-Tyrosine amide (1.0 g) was dissolved in 100 ml of 75% aqueous acetic acid and reduced with 0.5 g of 10% Pd/C at 50 p.s.i. for 15 hours. The catalyst was removed by filtration and the solution lyophilized to give 0.8 g. The material was dissolved in 7 ml water, filtered through a 3µ multipore filter, adjusted to pH 5 with NH$_4$OH(conc.) and chromatographed in an SP-C-25 column (2.5×100 cm) with 0.20 M NH$_4$OAc, pH 5.0, 100 ml/hr, 20 ml/tube. Tubes 71 to 78 were pooled and lyophilized to give 0.35 g of Arg-Sar-Asp-Sar-Tyr-NH$_2$.

TLC: R$_f$=0.23; n-BuOH/HOAc/H$_2$O 3/1/1; (Silica Gel GF); [α]D$^{21°}$ = +54.9 (C=0.091, 0.1 N HOAc).

EXAMPLE VI

Following the procedures of Examples I-V, but substituting for the protected sarcosine used therein an equivalent amount of suitably protected L-valine in Example I and an equivalent amount of suitably protected L-lysine in Example II, there is prepared H-ARG-LYS-ASP-VAL-TYR-NH$_2$

EXAMPLE VII

Following the procedures of Examples I-V but using equivalent amounts of the suitable starting materials, there are prepared:
H-VAL-TYR-NH$_2$
H-VAL-TYR-benzyl ester
H-SAR-TYR-benzyl ester
H-ARG-LYS-ASP-VAL-TYR-OH
H-ARG-LYS-GLU-VAL-TYR-OH
H-ARG-SAR-GLU-SAR-TYR-NH$_2$
H-ARG-LYS-GLU-VAL-TYR-NH$_2$
BOC-epsilon-CBZ-LYS-beta-benzyl-ASP-OH
BOC-epsilon-CBZ-LYS-gamma-benzyl-GLU-OH
BOC-SAR-gamma-benzyl-GLU-OH
BOC-epsilon-CBZ-LYS-beta-benzyl-ASP-VAL-TYR-OH-benzyl ester
BOC-epsilon-CBZ-LYS-gamma-benzyl-GLU-VAL-TYR-OH-benzyl ester
BOC-SAR-gamma-benzyl-GLU-SAR-TYR-NH$_2$

EXAMPLE VIII

Preparation of Fragment IVA:
H-beta-benzyl-ASP-VAL-TYR-benzyl ester, trifluoroacetate
(Beta-benzyl-L-Aspartyl-L-Valyl-L-Tyrosine benzyl ester, trifluoroacetate)

BOC-beta-benzyl-L-Aspartic acid and a molar equivalent of 1-hydroxybenzotriazole monohydrate are dissolved in dry DMF and the solution cooled to 0°. Then, a molar equivalent of dicyclohexylcarbodiimide is added to the solution and the whole is stirred for one hour at 0°. To the reaction mixture is then added a solution in DMF of a molar equivalent of triethylamine and L-Valyl-L-tyrosine benzyl ester, trifluoroacetate (prepared following the methods of Example I but substituting an equivalent amount of L-valine for the sarcosine used therein) and the whole is stirred overnight at ambient temperature. The product is isolated from the reaction mixture after reaction is complete and the BOC group is removed to yield the desired material.

EXAMPLE IX

Preparation of Fragment III (alternative):
BOC-epsilon-CBZ-LYS-beta-benzyl-ASP-VAL-TYR-benzyl ester
(BOC-epsilon-CBZ-L-Lysyl-beta-benzyl-L-Aspartyl-L-Valyl-L-Tyrosine benzyl ester)

BOC-epsilon-CBZ-L-Lysine hydroxysuccinimide is added to a solution of molar equivalents of triethylamine and beta-benzyl-L-Aspartyl-L-Valyl-L-Tyrosine benzyl ester trifluoroacetate in dry THF and the whole is stirred overnight. After the solids are removed, the product is isolated from the solution.

EXAMPLE X

Preparation of Fragment V:
tri-CBZ-ARG-epsilon-CBZ-LYS-OH
(tri-CBZ-L-arginine-epsilon-CBL-L-lysine)

To a suspension of tri-CBZ-L-Arginine para-nitrophenyl-ester (1.40 g, 2 mM) in 3 ml THF was added epsilon-CBZ-L-Lysine (625 mg 2.2 mM). Then triethylamine (450 mg 4.4 mM) was added and the while was stirred for 48 hours at ambient temperature. Following this, the solvent was removed under reduced pressure, and 20 ml of methanol was added to the resulting solid. After the methanol was filtered off and the solid was washed with a further 10 ml of methanol. The combined filtrate and wash was evaporated under reduced pressure to yield an oil, which was chromatographed on 10 ml silica gel using 0-5% methanol/chloroform as eluent. The second material which came off the column was the desired product as indicated by p.m.r.; yield 75 mg.

Anal: Calcd for C$_{44}$H$_{50}$N$_6$O$_{11}$.$\frac{2}{3}$CHCl$_3$: C, 58.41; H, 5.56; N, 9.15. Found: C, 58.88; H, 5.50; N, 9.29.

EXAMPLE XI

Preparation of pentapeptide (second alternative)

Molar equivalents of tri-CBZ-L-Arginyl-epsilon-CBZ-L-Lysine and 1-hydroxybenzotriazole are dissolved in dry DMF and a molar equivalent of dicyclohexylcarbodiimide is added with stirring. To this solution is added a solution of molar equivalents of beta-benzyl-L-Aspartyl-L-Valyl-L-Tyrosine benzyl ester trifluoroacetate and triethylamine in DMF and the whole is allowed to stir overnight. The product is isolated from the reaction mixture after removal of any solid residue, and the protective groups are removed to yield H-ARG-LYS-ASP-VAL-TYR-OH.

EXAMPLE XII

Following the procedures of Examples VIII-XI but employing equivalent amounts of suitable starting materials, there are prepared:
beta-benzyl-ASP-SAR-TYR-NH$_2$
gamma-benzyl-GLU-VAL-TYR-benzyl ester
gamma-benzyl-GLU-SAR-TYR-NH$_2$
BOC-SAR-beta-benzyl-ASP-SAR-TYR-NH$_2$
BOC-epsilon-CBZ-LYS-gamma-benzyl-GLU-VAL-TYR-benzyl ester
BOC-SAR-gamma-benzyl-GLU-SAR-TYR-NH$_2$
tri-CBZ-ARG-SAR-OH
ARG-SAR-ASP-SAR-TYR-NH$_2$
ARG-SAR-GLU-SAR-TYR-NH$_2$
ARG-LYS-ASP-VAL-TYR-OH
ARG-LYS-GLU-VAL-TYR-OH The pentapeptides prepared in the above examples all possess the same pharmacological activity as TP5, disclosed in the referenced patent and patent application.

The above examples have been provided by way of illustration and not to limit the scope of the subject application, which scope is defined by the appended claims.

I claim:
1. The protected tetrapeptide of formula alpha-T-X-omega-U-Z-Y-TYR-R', wherein:
   R' is OU or NH$_2$;
   X is epsilon-T''-LYS and Y is VAL or X and Y are both SAR;
   Z is ASP or GLU; and T and T'' are each a member selected from the group consisting of:
   (a)

wherein R$_1$ is phenyl; tolyl; xylyl; adamantyl; allyl; beta-cyanoethyl; fluorenylmethyl; benzyl, benzyl wherein the phenyl ring is substituted with from one to three members selected from halo, nitro, loweralkyl, and loweralkoxy, diisopropylmethyl;

diphenylmethyl; cyclohexyl; cyclopentyl; vinyl; t-butyl; t-amyl; dimethyltrifluoromethylmethyl; or dimethylbiphenylmethyl;

(b)

wherein $R_2$ is loweralkyl of two to four carbons or loweralkyl of one to four carbons substituted with from one to five halo groups;

(c)

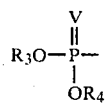

wherein V is S or O and $R_3$ and $R_4$ are each benzyl or loweralkyl;

(d)

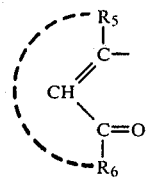

wherein $R_5$ and $R_6$ taken individually are each loweralkyl or $R_5$ and $R_6$ taken together is

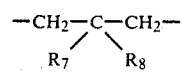

where $R_7$ and $R_8$ are each hydrogen or loweralkyl;

(e)

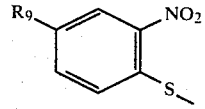

wherein $R_9$ is hydrogen or nitro; and (f)

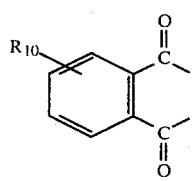

wherein $R_{10}$ is hydrogen, methyl, halo, or nitro provided that T is monodentate when X is SAR; and U is benzyl or benzyl in which the phenyl group is substituted with from one to three members each selected from halo, nitro, $C_1$-$C_3$ loweralkyl, and $C_1$-$C_3$ loweralkoxy.

2. The tetrapeptide of claim 1 which is alpha-T-SAR-omega-U-Z-SAR-TYR-R'.

3. The tetrapeptide of claim 2 which is BOC-SAR-beta-benzyl-ASP-SAR-TYR-R'.

4. The tetrapeptide of claim 1 which is alpha-T-epsilon-T'-LYS-omega-U-Z-VAL-TYR-R'.

5. The tetrapeptide of claim 4 which is BOC-epsilon-CBZ-LYS-beta-benzyl-ASP-VAL-TYR-R'.

6. The tetrapeptide of formula H-X-omega-U-Z-Y-TYR-R', wherein:

R' is OU or $NH_2$;

X is epsilon-T''-LYS and Y is VAL or X and Y are both SAR;

Z is ASP or GLU; T'' is a member selected from the group consisting of:

(a)

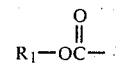

wherein $R_1$ is phenyl; tolyl; xylyl; adamantyl; allyl; beta-cyanoethyl; fluorenylmethyl; benzyl, benzyl wherein the phenyl ring is substituted with from one to three members selected from halo, nitro, loweralkyl, and loweralkoxy, diisopropylmethyl; diphenylmethyl; cyclohexyl; cyclopentyl; vinyl; t-butyl; t-amyl; dimethyltrifluoromethylmethyl; or dimethylbiphenylmethyl;

(b)

wherein $R_2$ is loweralkyl of two to four carbons or loweralkyl of one to four carbons substituted with from one to five halo groups;

(c)

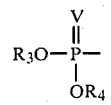

wherein V is S or O and $R_3$ and $R_4$ are each benzyl or loweralkyl;

(d)

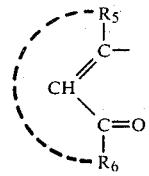

wherein $R_5$ and $R_6$ taken individually are each loweralkyl or $R_5$ and $R_6$ taken together is

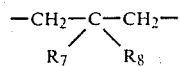

wherein $R_7$ and $R_8$ are each hydrogen or loweralkyl;

(e)

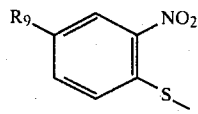

wherein $R_9$ is hydrogen or nitro; and (f)

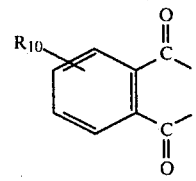

wherein $R_{10}$ is hydrogen, methyl, halo, or nitro; and U is benzyl or benzyl in which the phenyl group is substituted with from one to three members each selected from halo, nitro, $C_1$-$C_3$ loweralkyl, and $C_1$-$C_3$ loweralkoxy.

7. The tetrapeptide of claim 6 which is H-SAR-omega-U-Z-SAR-TYR-R'.

8. The tetrapeptide of claim 6 which is H-epsilon-CBZ-LYS-omega-U-Z-VAL-TYR-R'.

* * * * *